United States Patent [19]

Russell et al.

[11] Patent Number: 5,645,883
[45] Date of Patent: Jul. 8, 1997

[54] ZWITTERIONIC MATERIALS

[75] Inventors: Jeremy Colin Russell; Richard Neil Templar Freeman, both of Middlesex; Stephen Alexander Charles, Oxon, all of United Kingdom

[73] Assignee: Biocompatibles Limited, Middlesex, England

[21] Appl. No.: 464,677

[22] PCT Filed: Jan. 28, 1994

[86] PCT No.: PCT/GB94/00178

§ 371 Date: Jun. 7, 1995

§ 102(e) Date: Jun. 7, 1995

[87] PCT Pub. No.: WO94/16749

PCT Pub. Date: Aug. 4, 1994

[30] Foreign Application Priority Data

Jan. 28, 1993 [GB] United Kingdom ............... 9301701

[51] Int. Cl.$^6$ ................ B05D 3/02; A61L 27/00
[52] U.S. Cl. ...................... 427/2.25; 427/393.5
[58] Field of Search .............. 427/2.24, 2.25, 427/385.5, 393.5

[56] References Cited

FOREIGN PATENT DOCUMENTS

| | | |
|---|---|---|
| 0157469 | 1/1985 | European Pat. Off. . |
| 537972A1 | 4/1993 | European Pat. Off. . |
| WO86/02933 | 5/1986 | WIPO . |
| WO88/00956 | 2/1988 | WIPO . |
| WO92/06719 | 4/1992 | WIPO . |
| 9207858 | 5/1992 | WIPO . |
| WO92/07885 | 5/1992 | WIPO . |
| WO93/01221 | 1/1993 | WIPO . |
| WO93/05081 | 3/1993 | WIPO . |

*Primary Examiner*—Shrive Beck
*Assistant Examiner*—Erma Cameron
*Attorney, Agent, or Firm*—Sughrue, Mion, Zinn, Macpeak & Seas

[57] ABSTRACT

The present invention provides materials which comprise a surface having pendant zwitterionic groups Z comprising, as anion, a phosphate, sulphonate, carboxylate or phosphate-ester group or a phosphate ester group in which one or more of the ester oxygen atoms is replaced by —S—, —NH— or by a valence bond and, as cation, an ammonium, phosphonium or sulphonium moiety, provided that where the anion is a phosphate-ester group or derivative thereof or sulphonate and the cation is a trialkyl quaternary ammonium group (the alkyl groups each containing from 1 to 4 carbon atoms) and the group linking the anion and cation moieties is an alkylene group, the alkylene group, contains at least 5, preferably at least 6, and more preferably at least 7, carbon atoms. The materials have improved biocompatibility for instance as evidenced by reduced protein deposition and reduced platelet activation.

24 Claims, No Drawings

ZWITTERIONIC MATERIALS

The present invention relates to new materials which comprise a surface having pendent zwitterionic groups, processes for producing the materials, the use of compounds to provide such a material and to improve biocompatibility and to a device having such a surface. It also relates to new compounds useful in providing such materials.

Materials used in the manufacture of devices which, in use, come into contact with protein-containing or biological fluids must possess, as well as desirable physical and mechanical properties, good compatibility with protein-containing and/or biological fluids. Materials which do not possess such compatibility may for example promote the deposition of protein and, when brought into contact with blood, the activation of blood platelets which can have serious undesirable consequences such as the initiation of blood clotting. For example, materials which are used to produce contact lenses should desirably possess compatibility with the fluids in the eye which they come into contact with so as to reduce the deposition of protein upon them. Similarly, blood-contact devices, such as surgical implants and prostheses, should not lead to activation of blood platelets.

Several approaches have been used in the development of materials having good biocompatibility. One such approach has been to provide a surface having pendent groups which mimic the phospholipid zwitterionic groups which are found on the outside of cell surfaces. For example WO92/06719 and EP-A-32622 disclose natural and synthetic phospholipids which may be coated on a surface to provide improved biocompatibility and, in particular, haemocompatibility. Such phospholipids contain a phosphoryl choline head group, or a close analogue thereof. Further examples of materials which contain, at their surface, such head groups may be found in EP-A-157469, WO-A-86/02933, WO-A-88/00956, WO-A-91/13639, WO-A-92/07885, WO-A-92/07858, WO-A-92/21386 and WO-A-93/01221, and our as yet unpublished International patent application PCT/GB92/01580.

We have also found that compounds which contain such a phosphoryl choline headgroup or close analogue thereof, are able to reduce the tendency of microorganisms to adhere to and grow on surfaces. They may also be used more generally to reduce cellular adhesion at a surface. Materials which comprise such groups at their surface therefore have potentially wide utility wherever the growth of microorganisms such as bacteria, algae, yeast and fungi, particularly bacteria, occurs and is undesirable. Such compounds may therefore be used in both the medical field and also in other applications in industrial or domestic wherever it is desirable to prevent the growth of such microorganisms.

We have now found that compounds containing zwitterionic groups other than the naturally occurring phosphoryl choline groups and close analogues thereof, may also be used to improve the biocompatibility of a surface. In addition, such compounds may possess additional advantages over the use of compounds containing phosphoryl choline groups or close analogues thereof. For example, such compounds may possess improved solubility which renders them easier to treat a surface.

Accordingly, the present invention provides materials which comprise a surface having pendent zwitterionic groups Z comprising, as anion, a phosphate, sulphonate, carboxylate or phosphate-ester group or a phosphate ester group in which one or more of the ester oxygen atoms is replaced by —S—, —NH— or by a valence bond and, as cation, an ammonium, phosphonium or sulphonium moiety, provided that where the anion is a phosphate-ester group or derivative thereof or sulphonate and the cation is a trialkyl quaternary ammonium group (the alkyl groups each containing from 1 to 4 carbon atoms) and the group linking the anion and cation moieties is an alkylene group, the alkylene group, contains at least 5, preferably at least 6, and more preferably at least 7, carbon atoms;

with the exclusion of compounds which comprise a group of formula (I)

in which the groups —B are the same or different and each is —CH$_2$— or —C(=O)—, R$^1$ is hydrogen or alkyl of 1 to 12 carbon atoms or a group capable of bonding to, or bonded to, a ligand or R$^1$ is a polymerisable group and Z is such a zwitterionic group.

The excluded compounds containing a group of formula (I) have been excluded since they form the subject of a separate patent application filed under the title "New Materials" in our name on the same day as the present application, (the contents of which are incorporated herein by reference).

The invention also provides the use of compounds containing such zwitterionic groups in improving the biocompatibility of a surface. It thus relates to a method of improving the biocompatibility of a surface which comprises providing a surface having such pendent zwitterionic groups.

The invention further provides certain new compounds which contain such a zwitterionic group. In particular, the invention provides polymeric compounds comprising residues of a polymerisable compound containing a zwitterionic group Z and polymerisable compounds containing such a group useful as monomers to produce such polymers.

A material comprising a surface having such zwitterionic pendant groups may be provided by using a material the bulk and surface of which comprises such zwitterionic groups. Alternatively, zwitterionic groups may be provided by treating, for example coating, a substrate with one or more compounds containing such groups. Surface treatments such as this may be bound to the surface for example by physisorption, covalent bonding to reactive groups at a surface, or by ionic attraction. Preferably the pendant groups are provided by treating a substrate with one or more compounds containing zwitterionic groups rather than by forming a bulk material containing zwitterionic groups.

Materials comprising a surface having such zwitterionic pendant groups may be used in any application where it is desirable to provide a surface having good biocompatibility. This includes blood-contacting surfaces, contact lenses and other surfaces which come into contact with protein-containing and/or biological fluids as well as surfaces where it is desirable to avoid the growth of microorganisms and in particular bacteria.

In addition, materials comprising such surfaces may be used to provide means for the attachment of a variety of ligands to a material. The term ligand includes, but is not limited to, specific binding agents such as immunoglobulins and associated fragments thereof such as those useful for affinity separation and diagnostic applications, photosensitive and chemosensitive moieties such as those useful for detector and sensor applications and therapeutic agents, such as peptide fragments useful for clinical applications. Other ligands include peptide fragments which may be chemically linked to a surface, such as fragments which induce cell attachment and may therefore be used to allow cell seeding at the surface.

Means for the attachment of such ligands may be provided by compounds containing the zwitterionic group or, alternatively, they may be provided by additional compounds attached to the surface as well as compounds containing the zwitterionic group. In particular, means for the attachment of such ligands may be provided by groups which contain an amine, hydroxyl or carboxylic acid group, or an activated derivative thereof. Such groups may optionally be in the form of a suitable salt and may, where necessary, be attached to a spacer group, such as alkylene of 1 to 12 carbon atoms, of sufficient length to allow the reactive group to interact with its binding partner on the ligand.

It will be appreciated that where it is desired to control the number of sites of attachment of such a ligand to a surface then a mixture may be used of compounds containing a zwitterionic group Z suitable for attachment to a ligand and containing a zwitterionic group Z not suitable for such attachment. Alternatively a copolymer of two such polymerisable compounds one of which contains a zwitterionic group Z and one of which provides a site for attachment of a ligand, may be used.

Zwitterionic groups Z

Preferably the group linking the anion and cation moieties of the zwitterionic group contains at least 2, preferably at least 5 carbon atoms and up to 20, more preferably up to 10 carbon atoms.

Where the zwitterionic group contains an alkylene group linking the anion and the cation moieties of the zwitterionic group, preferably such a group contains at least 6, and for instance at least 7 carbon atoms. For example such a group contains at least 8, carbon atoms.

As examples of zwitterionic groups which may be used in the method of the present invention (hereinafter designated groups Z) mention is made of groups of Types A–D below. Of those, groups of type A are preferred:

Type A

In one specific embodiment, the zwitterionic group Z comprises as anion a phosphate ester, or a phosphate ester group in which one or more of the ester oxygen atoms is replaced by —S—, —NH— or a valence bond, and as cation an ammonium moiety, preferably a quaternary ammonium moiety, and a group linking the anionic and cationic moieties which comprises at least 5, preferably at least 6, for instance at least 7, carbon atoms if it is an alkylene group.

Such groups are preferably of the formula (II)

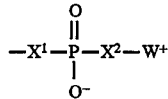
(II)

in which the moieties $X^1$ and $X^2$, which are the same or different, are —O—, —S—, —NH— or a valence bond, preferably —O—, and $W^+$ is a group comprising an ammonium, phosphonium or sulphonium cationic group and a group linking the anionic and cationic moieties which, if the cation is an ammonium cation and the linking group is an alkylene group comprises at least 6, for instance at least 7, carbon atoms.

Preferably W contains as cationic group an ammonium group, more preferably a quaternary ammonium group.

The group $W^+$ may for example be a group of formula —$W^1$—$N^+R^3_3$, —$W^1$—$P^+R^{3a}_3$, —$W^1$—$S^+R^{3a}_2$ or —$W^1$—$Het^+$ in which:

$W^1$ is alkylene of 5 or more, preferably at least 6, for instance at least 7 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either the groups $R^3$ are the same or different and each is hydrogen or alkyl of 1 to 4 carbon atoms, preferably methyl, or aryl, such as phenyl or two of the groups $R^3$ together with the nitrogen atom to which they are attached form a heterocyclic ring containing from 5 to 7 atoms or the three groups $R^3$ together with the nitrogen atom to which they are attached form a fused ring structure containing from 5 to 7 atoms in each ring, and optionally one or more of the groups $R^3$ is substituted by a hydrophilic functional group, and the groups $R^{3a}$ are the same or different and each is $R^3$ or a group $OR^3$, where $R^3$ is as defined above; or Het is an aromatic nitrogen-, phosphorus- or sulphur-, preferably nitrogen-, containing ring, for example pyridine.

Compounds in which one or more of the groups $R^3$ are substituted by a hydrophilic group are particularly suitable for providing a surface with an increased water content. Suitable functional groups include hydroxy, amine and carboxyl groups. Preferably however $R^3$ is not substituted by such groups.

Alternatively, $W^+$ may itself be a heterocyclic group containing a nitrogen, phosphorus or sulphur atom, for example a heterocycle containing from 5 to 7 atoms, preferably including a quaternised nitrogen atom.

Where $W^+$ is a group —$W^1$—$N^+R^3_3$, —$W^1$—$P^+R^{3a}_3$, —$W^1$—$S^+R^3_2$ or —$W^1Het^+$ preferably the group $W^1$ contains up to 20 carbon 1 +atoms, more preferably up to 12 carbon atoms. Preferably where $W^1$ contains 6 or more carbon atoms where the cation is a group —$NR^{33}$, and otherwise preferably $W^1$ contains 2 or more carbon atoms.

Preferably $W^1$ is a straight-chain alkylene group.

Where $W^1$ contains a cycloalkyl group, preferably the cycloalkyl group contains from 5 to 7, more preferably 6, carbon atoms in the ring. Where $W^1$ contains an aryl group this may for example be phenyl unsubstituted or substituted by for example one or more alkyl groups of 1 to 4 carbon atoms.

Compounds containing a group of formula (II) may be obtained by the reaction of an analogous compound containing a group of formula (IIA)

(IIA)

in which $W^1$ $X^1$ and $X^2$ are as hereinbefore defined, L is a displaceable leaving group, such as halogen, alkylsulphonyloxy or arylsulphonyloxy with a compound of formula $NR^3_3$, $PR^{3a}$, $SR^3_2$ or Het where $R^3$ and Het are as defined above. The reaction is generally performed in an organic solvent, such as chloroform or acetonitrile and at a temperature from room temperature to 120° C., for example in a sealed vessel.

Compounds containing a group of formula (IIA) may be obtained by the adaptation of known methods.

Alternatively, compounds containing a group of formula (II) in which $W^+$ is —$W^1$—$N^+R^3_3$, —$W^1$—$P^+R^{3a}_3$ or —W$^1$—S$^+$R$^3_2$, may be obtained by derivatisation, for example by reaction with an alkyl halide, of a corresponding compound bearing a group —W$^1$—NR$^3_2$, —W$^1$—PR$^{3a}_2$ or —W$^1$—SR$^3$ in place of W. The reaction may for example be carried out in the presence of a base, such as potassium carbonate, in an organic solvent such as dichloromethane at a temperature from 0° to 50° C.

Compounds bearing a group —W$^1$—NR$^3_2$, —W$^1$—PR$^{3a}_2$ or —W$^1$—SR$^3$ may be obtained by adaptation of known methods.

Type B

Further Examples of the zwitterionic groups Z which may be used in the method of the present invention are groups of formula (III)

$$—X^3—R^4—N^+(R^5)_2—R^6—V \qquad (III)$$

in which X$^3$ is a valence bond, —O—, —S— or —NH—, preferably —O—;

V is a carboxylate, sulphonate or phosphate anion;

R$^4$ is a valence bond (together with X$^3$) or alkylene —C(O)alkylene- or —C(O)NHalkylene preferably alkylene and preferably containing from 1 to 6 carbon atoms in the alkylene chain;

the groups R$^5$ are the same or different and each is hydrogen or alkyl of 1 to 4 carbon atoms or the groups R$^5$ together with the nitrogen to which they are attached form a heterocyclic ring of 5 to 7 atoms; and R$^6$ is alkylene of 1 to 20, preferably 1 to 10, more preferably 1 to 6 carbon atoms provided that when V is a sulphonate anion, R$^6$ is alkylene of 6 or more carbon atoms.

Compounds containing a group of formula (III) in which R$^4$ and X$^3$ are together a valence bond, may be obtained by reaction of a compound of formula R$^5_2$NR$^6$V with an appropriate derivative. Compounds containing a group of formula (III) in which R$^4$ is other than a valence bond may be obtained using spacer chemistry according to standard methods, using an ether (or sulphide or secondary amine), ester (thioester or amide) or carbonate (thiocarbonate or urea derivative). This may include the use of a Michael acceptor (for example an acrylate) which undergoes reaction with secondary amines (for example N-methylglycine) to give a tertiary amine and is then alkylated to give the final product.

Type C

Further examples of zwitterionic groups Z which may be used in the method of the present invention are the groups of formula (IV)

$$—X^4—R^7—\underset{\underset{^+NR^8_3}{|}}{C}HCO_2^- \qquad (IV)$$

in which X$^4$ is a valence bond, —O—, —S— or preferably —O—,

R$^7$ is a valence bond (optionally together with X$^4$) or alkylene, —C(O)alkylene- or —C(O)NHalkylene, preferably alkylene and preferably containing from 1 to 6 carbon atoms; and the groups R$^8$ are the same or different and each is hydrogen or alkyl of 1 to 4 carbon atoms, preferably methyl, or two of the groups R$^8$, together with the nitrogen to which they are attached, form a heterocyclic ring of from 5 to 7 atoms, or the three group R$^8$ together with the nitrogen atom to which they are attached form a fused ring structure containing from 5 to 7 atoms in each ring.

Compounds containing a group of formula (IV) may be obtained by reacting an appropriate derivative with a compound of formula (IVA)

$$L^1—X^4—R^7—CH(N^+R^8_3)CO_2^- \qquad (IVA)$$

wherein X$^4$ R$^7$ and R$^8$ are defined in relation to formula (IV) and L$^1$ is a carboxylic acid or activated derivative thereof.

Type D

Further examples of the zwitterionic group Z which may be used in the method of the present invention are the groups of formula (V)

$$—X^5—R^9—(U^-)—R^{10}—W^{2+} \qquad (V)$$

in which X$^5$ is —O—, —S—, —NH—, —OC(O)—, —NHC(O)—, or —SC(O)—, R$^9$ and R$^{10}$ are the same or different and each is alkylene of 1 to 20, preferably 1 to 10 carbon atoms, U is carboxylate, phosphate, sulphate or oxime and W$^{2-}$ is a ammonium, phosphonium or sulphonium, preferably ammonium group.

Preferably X$^5$ is —OC(O)—, —NHC(O)— or —SC(O)—, more preferably —OC(O)—.

Compounds containing a group of formula (V) may be obtained by the reaction of an amine, phosphine or sulphide W$^2$ with a corresponding compound containing a group of formula (VA)

$$—X^5—R^9—C(U^-)—R^{10}—Hal \qquad (VA)$$

in which X$^5$, U, R$^9$ and R$^{10}$ are as hereinbefore defined and Hal is halogen.

Compounds containing a group of formula (VA) in which U is oxime may be obtained from the corresponding compound bearing a carbonyl group in place of U and compounds in which U is phosphate or sulphate may be obtained by reaction of a corresponding compound bearing a hydroxyl group in place of the group U with a phosphorous oxychloride or sulphonylchloride followed by hydrolysis. Compounds bearing hydroxyl or carbonyl in place of the group U may be obtained by adaptation of known methodology.

Compounds Containing a Zwitterionic Group Z

Particular types of compounds containing a zwitterionic group Z will now be described. Such compounds are provided as an additional feature of the present invention.

A.1 Phospholipid Analogues containing a zwitterionic group Z

A-1.1 One type of compound provided by the present invention is analogues of fatty acid diesters of phosphatidyl choline, comprising a group of formula (VI):

$$\begin{array}{l} H_2C—Z \\ | \\ —CH \\ | \\ —CH_2 \end{array} \qquad (VI)$$

These analogues include saturated and unsaturated ester and ether derivatives of fatty acids. Mixed esters or ethers may be used. Preferably the fatty side chains will be straight as opposed to branched and preferably contain from 12 to 20 carbon atoms.

Analogues of dipalmitoyl phosphatidyl choline (DPPC) and dimyristoyl phosphatidyl choline (DMPC), preferably containing an extended zwitterionic phosphate amine group Z, and mixtures thereof, are preferred.

Phospholipid analogues containing a group of formula (VI) may be used to coat hydrophobic substrates such as PVC, polyethylene or polypropylene. The coating may be applied using a solution of the phospholipid analogue in an organic solvent and the solvent subsequently removed to leave a coating of phospholipid analogue which is believed to be adhered to the substrate by physisorption. This technique is described in more detail in our patent application WO-A-92/06719 the contents of which are incorporated herein by reference.

A1.2 The present invention further provides diacetylenic phospholipids of the formula (VII)

in which Z is a zwitterionic group as hereinbefore defined and wherein at least one of $Q^1$ and $Q^2$ is a group of the formula (VIII)

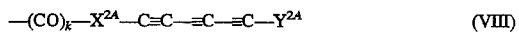

wherein k is 0 or 1, $X^{2A}$ is an aliphatic or cycloaliphatic group, $Y^{2A}$ is H or a monovalent aliphatic or cycloaliphatic group, the total number of carbon atoms in $X^{2A}$ and $Y^{2A}$ in each $Q^1$ and/or $Q^2$ being 8 to 26, preferably 20 to 26, and the other of $Q^1$ and $Q^2$ is either (a) the same or a different group of formula (VIII) or (b) is an aliphatic or cycloaliphatic group containing at least 8 carbon atoms. Preferably $Q^1$ and $Q^2$ are the same and are both groups of formula (VIII).

Most preferred compounds of formula (VII) are analogues of 1,2-dipentacosanoyl-10,12-diyne-sn-glycero-3-phosphorylcholine (DAPC), in which the phosphoryl choline group is replaced by a zwitterionic group Z, preferably an extended zwitterionic phosphate-amine group.

Compounds of formula (VII) may be obtained by adaptation of the methods described in our earlier patent application, EP-A-32622, the content of which are incorporated herein by reference. They are suitable for coating hydrophobic substrates and after coating may be crosslinked intramolecularly or intermolecularly for example by irradiation as is described in EP-A-32622.

Alternatively compounds of formula (VII) may be pre-polymerised by intermolecular crosslinking so that an oligomer of a compound of formula (VII) is used to treat the substrate. This pre-polymerisation may be performed by analogy with the process is described in our earlier application WO-A-92/21386. the contents of which are incorporated herein by reference.

A.2 Non-Polymeric Compounds Containing a Zwitterionic Group Z

Other compounds provided by the present invention are of formula (IX):

wherein $Y^A$ is a reactive group which can form a covalent bond with a reactive group on the surface of a material and Z is a zwitterionic group as hereinbefore defined.

As examples of the reactive group $Y^A$ there may be mentioned groups which will react with surface hydroxyl groups of a material, for instance halogen, haloalkyl, halodialkylsilyl, halo(dialkyl)silylalkyl, aminoalkyl and activated aminoalkyl groups. Compounds containing a phosphoryl choline zwitterionic group are described in more detail in EP-A-157469 (incorporated herein by reference); compounds of formula (IX) may be obtained by analogy with the methods described therein.

A2.1 Among the compounds of formula (IX), an especially preferred group of compounds are those of formula (X):

in which Z is as hereinbefore defined, $W^A$ is hydrogen or $—NHW^A$ is an activated amine group capable of reacting with a surface, and $X^A$ is a straight or branched $C_{1-20}$ alkylene group, preferably a group of formula $—(CH_2)_b—$, or $X^A$ is a group of formula $—(CH_2CH_2O)_c—$, or $—(CH_2)_d—Ar—(CH_2)_e—$ where b is from 1 to 20, c is from 1 to 20, d and e are the same or different and each is from 0 to 5, and Ar is a para- or meta- disubstituted phenyl group (preferably a para-disubstituted phenyl group) which is optionally further substituted by one or more $C_1-C_4$ alkyl groups, or an acid addition salt thereof or a hydrate thereof.

Where $—NHW^A$ is an activated amine group capable of reacting with a surface, preferably $W^A$ is:

a group B—C(O)— where B is halogen, an alkyl group, preferably containing one to four carbon atoms, unsubstituted or substituted by one or more electron withdrawing substituents, a phenyl or 5- or 6-membered heteroaromatic ring containing from 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents;

a group $B^1$—OC(O)— where $B^1$ is an alkyl group, preferably containing one to four carbon atoms, unsubstituted or substituted by one or more electron withdrawing substituents or is a phenyl or 5- or 6-membered heteroaromatic ring containing i to 3 nitrogen atoms, optionally fused with a further phenyl ring or 5- or 6-membered heteroaromatic ring containing 1 to 3 nitrogen atoms and unsubstituted or substituted by one or more electron withdrawing substituents; or a phenyl or 5- or 6-membered heteroaromatic ring containing 1 to 3 nitrogen atoms optionally fused with a further phenyl ring or 5- or 6-membered heteroaromatic ring containing 1 to 3 nitrogen atoms and unsubstituted or substituted by one or more electron withdrawing substituents.

Suitable electron withdrawing substituents, which may be present in the group $W^A$, include halogen, nitro and cyano.

Where the group $W^A$ contains a heteroaromatic ring, preferably the heteroaromatic ring is an imidazole or 1,3,5-benzotriazole.

Particularly preferred compounds containing a group of formula (X) are those in which $X^A$ is $—(CH_2)_b—$ and b is from 1 to 8, especially 2 to 6. Other preferred compounds are those wherein $X^A$ is $—(CH_2CH_2O)_c—$ and c is from 1 to 7.

In one specific embodiment of compounds of formula (X), Z is a group of formula (II), as hereinbefore defined, in which if the cationic moiety is an ammonium ion and the group linking the cationic and anionic moieties is an alkylene group, the alkylene contains at least 7, preferably at least 8 carbon atoms.

Compounds containing a group of formula (X) may be prepared by adaptation of the methods described in our earlier patent application WO-A-92/07858 the contents of which are incorporated herein by reference. The compounds are suitable for treating a substrate having reactive groups at the surface, such as carboxyl, hydroxyl, amino or thiol groups, if necessary using a prior activation of the substrate. The compounds may be used in analogous manner to those disclosed in WO-A-92/07858.

A2.2 Further preferred compounds of formula (IX) which may be used to treat the surfaces of synthetic polymers are those in which the group $Y^A$ is a group —$(CH_2)_e V^A$, —$(CH_2)_f$—Ar—$(CH_2)_g V^A$, —$(CH_2CH_2O)_h V^A$ or —$CH_2$—$CHV^A$—$CH_2 V^A$ wherein e is from 1 to 30, Ar is a para- or meta-disubstituted aryl or heteroaryl group;
f and g are the same or different and each is from 0 to 5, and f+g is from 1 to 10;
h is from 1 to 20 and
$V^A$ is a group which reacts with functional groups of the polymer.

Preferably in such compounds $V^A$ is: an epoxide group; a group

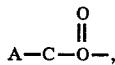

where A is $C_{1-4}$ straight or branched alkyl optionally substituted with one or more electron withdrawing groups or A is an optionally substituted aromatic or heteroaromatic ring system;
a group $T^1$—$SO_3$—
where $T^1$ is a straight chain alkyl of 1 to 4 carbon atoms optionally substituted by alkyl or alkoxy of 1 to 4 carbon atoms or halogen or an optionally substituted aromatic or heteroaromatic ring system;
a group

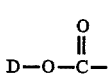

where D is an optionally substituted aromatic or heteroaromatic ring system or an N-substituted imide derivative;
a group

where E is a halogen atom, or an N-substituted nitrogen-containing heteroaromatic ring system; or
a group of formula R'C(O)OC(O)—, where R' is a group Z—$(CH_2)_e$—, Z—$(CH_2CH_2O)_h$— or Z—$(CH_2)_f$—Ar—$(CH_2)_g$—
where Z is a zwitterionic group as hereinbefore defined, e, f, g, and h are as hereinbefore defined, or R' is an alkyl group preferably of 1 to 4 carbon atoms, optionally substituted by alkyl or alkoxy of 1 to 4 carbon atoms or halogen or is an optionally substituted aromatic or heteroaromatic ring system.

These compounds may be obtained by adaptation of the methods described in our earlier patent application WO-A-91/13639, the contents of which are incorporated herein by-reference.

These compounds are particularly suitable for treating polymer substrates having free reactive hydroxyl, carboxyl, or amino groups. In other cases it may be necessary to activate the substrate prior to reaction with these compounds using Known etching or derivatising techniques. It may also be desirable in certain cases to provide spacer groups between the polymer and the residue of the compound of formula (II). The compounds may be used in an analogous manner to that described in WO-A-91/13639.

A2.3 Further compounds of the formula (IX) which may be mentioned are thiol and disulphide compounds in which the reactive group $Y^A$ is a group of formula (XI)

in which $X^{14}$ is a straight or branched $C_{1-20}$ alkylene group, preferably a group of formula —$(CH_2)_{ba}$—, or $X^{14}$ is a group of formula —$(CH_2CH_2O)_{ca}$—, or —$(CH_2)_{da}$—Ar—$(CH_2)_{ea}$— where ba is from 1 to 20, ca is from 1 to 20, da. and ae are the same or different and each is from 0 to 5, and Ar is a para- or meta- disubstituted aryl group such as a phenyl, biphenyl or naphthyl group (preferably a para-disubstituted biphenyl group) which is optionally further substituted by one or more $C_1$–$C_4$ alkyl groups; and either
$T^A$ is a valence bond or a divalent functional or heterocyclic group; and
$U^A$ is hydrogen or a group —$SU^{14}$ where $U^{14}$ is an alkyl, cycloalkyl, alkylcycloalkyl, aryl, alkylaryl, heterocyclic, alkylheterocyclic group or a group —$T^A$—$X^{14}$—Z, where Z is a zwitterionic group as hereinbefore defined; or
$T^A$ is a trivalent alkylene group, and
$U^A$ is a group —$SU^{14}$ and $U^{14}$ is an alkylene group, unsubstituted or substituted by alkyl, aryl, alkylaryl, cycloalkyl or alkylcycloalkyl groups and bonded to the group $T^a$ so —$T^A$—S—S—$U^{14}$ form a 5 to 8 membered, preferably 5 or 6 membered, ring containing a disulphide linkage;
or a hydrate thereof.

Compounds in which $Y^A$ is a group of formula (XI) are particularly useful for the treatment of metal, e.g. silver, substrates. Their use is described in more detail in our UK patent application 9224031.6 filed Nov. 16, 1992, the contents of which are incorporated herein by reference.

B. Polymeric compounds containing a zwitterionic group Z

As a further feature the present invention provides polymeric compounds comprising residues of a polymerisable, compound containing a zwitterionic group Z.

It relates in particular to polymers which are obtainable by polymerising or copolymerising a polymerisable, compound containing a zwitterionic group Z, and to polymers which are obtainable by grafting, e.g. polymerisation grafting, a compound containing a zwitterionic group Z, e.g. a polymerisable compound, onto a polymer substrate.

The polymer may be homopolymers or copolymers of a polymerisable compound containing a zwitterionic group Z. Alternatively a polymeric compound containing such groups may be a polymer onto which the zwitterionic groups Z have been grafted.

Such polymers may for example be condensation polymers such as polyesters, polyurethanes or polymers of ethylenically unsaturated compounds, such as polyolefins, poly(alk)acrylates for example polyacrylates or polymethacrylates, polystyrenes or polyvinyl polymers.

The invention also relates to polymerisable, preferably ethylenically unsaturated, compounds containing a zwitterionic group Z.

B1 one such type of polymeric compound, is a polymer obtainable by copolymerising a polymerisable, preferably ethylenically unsaturated, comonomer containing a zwitterionic group Z and a comonomer containing a group capable of binding the copolymer to a surface or by polymerising a polymerisable, preferably ethylenically unsaturated, monomer containing both a zwitterionic group Z and a group capable of binding the polymer to a surface. Such polymers which may be used to coat a surface of a substrate.

Such polymers therefore comprise either:

residues of a polymerisable, preferably ethylenically unsaturated, comonomer containing a zwitterionic group Z and of a comonomer containing a group capable of binding the polymer to a surface, or;

residues of a monomer containing both a zwitterionic group Z and a group capable of binding the polymer to a surface.

Preferably such copolymers contain residues of one or more comonomer derivatives of acrylic acid, alkacrylic acid or styrene of formula (XII) or (XIII),

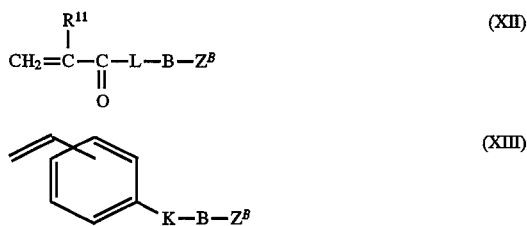

in which $R^{11}$ is hydrogen or a $C_1$–$C_4$ alkyl group;

L is —O— or —$NR^{12}$— where R is hydrogen or a $C_1$–$C_4$ alkyl group or $R^{12}$ is —B—$Z^B$ where B and $Z^B$ are as defined below;

K is a group —$(CH_2)_pOC(O)$—, —$(CH_2)_pC(O)O$—, —$(CH_2)_pOC(O)O$—, —$(CH_2)_pNR^{13}$—, —$(CH_2)_pNR^{13}C(O)$—, —$(CH_2)_pC(O)NR^{13}$—, —$(CH_2)_pNR^{13}C(O)O$—, —$(CH_2)_pOC(O)NR^{13}$—, —$(CH_2)_pNR^{13}C(O)NR^{13}$—, (in which the groups $R^{13}$ are the same or different) —$(CH_2)_pO$—, —$(CH_2)_pSO_{13}$—, or, optionally in combination with B, a valence bond and p is from 1 to 12 and $R^{13}$ is hydrogen or a $C_1$–$C_4$ alkyl group;

B is a straight or branched alkylene, oxaalkylene or oligo-oxaalkylene chain, preferably containing up to 12 carbon atoms, optionally containing one or more fluorine atoms up to and including perfluorinated chains or, if $Z^B$ contains a carbon-carbon chain between B and the centre of permanent positive charge or if L or K contains a terminal carbon atom bonded to B, a valence bond;

and $Z^B$ is a zwitterionic group Z.

In particular $Z^B$ may be a group of formula (XIV), (XV) or (XVI).

The groups of formulae (XIV), (XV) and (XVI) are:

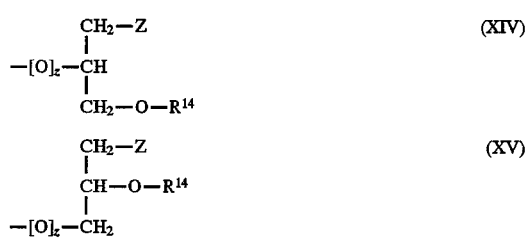

wherein Z is as hereinbefore defined, $R^{14}$ is hydrogen or a group of formula —$C(O)B^1R^{14a}$ where $R^{14a}$ is hydrogen or methyl preferably methyl, $B^1$ is a valence bond or straight or branched alkylene, oxalkylene or oligo-oxaalkalyene group, preferably containing up to 12 carbon atoms; and if B is other than a valence bond, z is 1 and if B is a valence bond, z is 0, when the group of formula (XIV), (XV) or (XVI) is directly bonded to an oxygen or nitrogen atom and otherwise z is 1.

The proviso on whether B may be a valence bond ensures that the group of formula (I) is not directly bonded to a heteroatom, such as an oxygen or nitrogen atom.

More preferably however $Z^B$ is a group Z as hereinbefore defined.

Such copolymers further comprise the residues of comonomers containing groups capable of binding the copolymer to a surface by physisorption, or by covalent binding to a reactive group at the surface. Specific examples of these comonomers are compounds of formulae (XVIIA) and (XVIIB)

wherein $R^{15}$ is hydrogen or a $C_{1-4}$ alkyl group;

$L^1$ is —O— or —$NR^{16}$— where $R^{16}$ is hydrogen or a $C_{1-4}$ alkyl group or $R^6$ is —G as defined below:

$K^1$ is a group —$(CH_2)_qOC(O)$—, —$(CH_2)_qC(O)$—, —$(CH2)_qOC(O)O$—, —$(CH_2)_qNR^{17}$—, —$(CH_2)_qNR^{17}C(O)$—, —$(CH_2)_qC(O)NR^{17}$—, —$(CH_2)_qNR^{17}C(O)O$—, —$(CH_2)_qOC(O)NR^{17}$—, —$(CH_2)_qNR^{17}C(O)NR^{17}$—, (in which the groups $R^{17}$ are the same or different) —$(CH_2)_qO$—, —$(CH_2)_qSO_3$—, or, optionally in combination with B, a valence bond and q is from 1 to 12 and $R^{17}$ is hydrogen or a $C_1$–$C_4$ alkyl group, and G is a) a reactive group capable of covalently binding to a surface;

b) a group capable of binding to a surface by physisorption; or c) an ionic group capable of binding to a surface by ionic interaction.

In the case a), G may be for instance an alkylene, oxalkylene or oligo-oxaalkylene chain, preferably containing up to 12 carbon atoms, terminating in a reactive group such as aldehyde, hydroxyl, amino, carboxyl, epoxy, —$CHOHCH_2Hal$ (in which Hal is a halogen atom such as chlorine, bromine or iodine), succinimido, tosylate, such as 2(N-methylpyridinium tosylate), triflate, imidazole carbonyl-amino or an optionally substituted triazine.

Alternatively, in compounds of formula (XVIIA) —$L^1$—G may be a hydroxyl group; such compounds are acrylic or alkacrylic acids.

In addition the residues of such comonomers may be used to provide crosslinkable groups in the polymer. Such comonomers may also provide means for the attachment of a ligand to the polymer, either before, or more preferably after, using the polymer to treat a surface.

In the case b) G may for instance be an alkyl, alkoxy-alkyl or (oligo-alkoxy)alkyl group containing 6 or more, preferably 6 to 24, carbon atoms, or an alkyl, alkoxy-alkyl or (oligo-alkoxy)alkyl group substituted by one or more fluorine atoms and preferably containing 6 or more, more preferably 6 to 24 carbon atom, or G may be a siloxy group typically containing from 1 to 50, preferably from 5 to 30 silicon atoms.

In the case c) G may for instance be a carboxylate, sulphonate, hydrogenphosphate or phosphate group when the surface has a cationic surface charge or a quaternary ammonium or phosphonium group where the surface has an anionic surface charge.

Such copolymers may further comprise the residues of one or more diluent comonomers.

Particular examples of diluent comonomers include alkyl (alk)acrylate preferably containing 1 to 4 carbon atoms in the alkyl group of the ester moiety, such as methyl (alk) acrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl (alk)acrylate; an alkyl (alk) acrylamide preferably containing 1 to 4 carbon atoms in the alkyl group of the amide moiety; a hydroxyalkyl (alk) acrylate preferably containing from 1 to 4 carbon atoms in the hydroxyalkyl moiety, e.g. a 2-hydroxyethyl (alk) acrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comonomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Particularly suitable diluent comonomers include methacryloyl glucose or sorbitol methacrylate.

It is to be understood that throughout the specification (alk)acrylate, (alk)acrylic and (alk)acrylamide mean acrylate or alkacrylate, acrylic or alkacrylic and acrylamide or alkacrylamide respectively. Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth) acrylamide shall be understood to mean acrylate or methacrylate, acrylic or methacrylic and acrylamide or methacrylamide respectively.

Alternatively polymers may be used which comprise residues of compounds of formula (XII) or (XIII) in which the group —$Z^1$ is a group of formula (XIV), (XV) or (XVI) but where —$B^1$ is a group capable of binding to a surface by physisorption such as alkylene, oxaalkylene or oligo-oxaalkylene, optionally substituted by one or more fluorine atoms and preferably containing up to 24, more preferably from 6 to 18 carbon atoms or a siloxane group. such monomers contain both a zwitterionic group Z and a group capable of bonding to a surface by physisorption, and may be used in homopolymers or in copolymers with other comonomers either containing a zwitterionic group Z such as those of formula (XII) or (XIII) or capable of providing physisorption such as those of formula (XVIIA) or (XVIIB) and/or optionally one or more diluent comonomers.

It will be appreciated that polymers or copolymers containing groups capable of binding to a surface by physisorption are particularly suitable for treating hydrophobic surfaces. Similarly copolymers containing groups capable of covalently binding to a surface are suitable for binding to surface having reactive groups such as hydroxyl, carboxyl or amino groups; such surfaces are generally hydrophilic.

Polymers and copolymers containing residues of a polymerisable compound containing a zwitterionic group Z may be obtained by conventional polymerisation techniques. Such techniques are for example described in our earlier patent application WO-A-93/01221, the contents of which are incorporated herein by reference. Where the polymer comprises residues of cross-linkable groups, then polymerisation will be carried out under conditions so as not to produce cross-linking. The polymer may be used to treat a surface in the manner described in the above application and, where the polymer comprises such cross-linkable groups it may then be cross-linked in conventional manner. The monomers of formula (XII) and (XIII) may be obtained by the adaptation of conventional methods.

The present invention further provides a polymer blend comprising such a polymer comprising residues of a compound containing a zwitterionic group Z and a polymer having desirable physical and/or mechanical properties. Such blends may combine improved biocompatibility from the zwitterionic polymers with the desirable physical and/or mechanical properties of the other polymer. Such blended materials may be produced using conventional methodology and may be used as bulk materials rather than surface coatings to fabricate devices with improved biocompatibility.

B2 Further polymers of the invention are polymers obtainable by grafting a polymer with a compound containing a zwitterionic group Z onto a polymer substrate. Where necessary an intermediate binding group may be used which is first grafted onto the polymer and then reacts with the compound containing the zwitterionic group.

Compounds which may be used to graft a zwitterionic group Z onto a polymer include compounds of formula (XVIII)

$$Y^{3B}-X^{3B}-Z \quad \quad (XVIII)$$

in which Z is as hereinbefore defined, $X^{3B}$ is an aryl or a straight or branched $C_1$-$C_{20}$ alkylene group, optionally containing one or more carbon-carbon double or triple bonds, ether linkages or aryl groups; the aryl groups being unsubstituted or substituted by one or more $C_{1-4}$ alkyl groups; and $Y^{3B}$ is a reactive group.

For example $Y^{3B}$ may be an amino or hydroxyl group, a group HOCH$_2$CH(OH)— (in which case $X^{3B}$ is preferably —CH$_2$—, so that the compound containing the zwitterionic group Z is a glycerol-derivative) or an imidazole group.

Alternatively $Y^{3B}$ may be a polymerisable group capable of polymerisation initiated by a radical forming linking group bound to the polymer. Where $Y^{3B}$ is such a group then the compound of formula (XVIII) may be a compound of formula (XIX) or (XX):

$$CH_2=C-\underset{\underset{O}{\|}}{C}-L-X^{3B}-Z \quad \quad (XIX)$$
$$\phantom{CH_2=}\overset{R^{18}}{|}$$

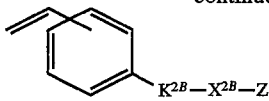 (XX)

in which Z is as hereinbefore defined, $X^{3B}$ is defined in relation to formula (XVIII) and $R^{18}$ is hydrogen or a $C_1$-$C_4$ alkyl group;

$L^2$ is —O— or —$NR^{19}$— where $R^{19}$ is hydrogen or a $C_1$-$C_4$ alkyl group or $R^{19}$ is —$X^{3B}$—Z where $X^{3B}$ and Z are as defined above; and $K^{2S}$ is a group —$(CH_2)_r OC(O)$—, —$(CH_2)_r C(O)O$—, —$(CH_2)_r OC(O)O$—, —$(CH_2)_r NR^{20}$—, —$(CH_2)_r NR^{20}C(O)$—, —$(CH_2)_r C(O)NR^{20}$—, —$(CH_2)_r NR^{20}C(O)O$—, —$(CH_2)_r OC(O)NR^{20}$—, —$(CH_2)_r NR^{20}C(O)NR^3$—, (in which the groups $R^{20}$ are the same or different) —$(CH_2)_r O$—, —$(CH_2)_r (SO_3$—, or a valence bond and r is from 1 to 12 and $R^{20}$ is hydrogen or a $C_1$-$C_4$ alkyl group.

Compounds such as those of formula (XVIII) may be used to treat polymers such as polyurethanes, hydroxyethyl methacrylates and hydroxyethyl methacrylate/methacrylic acid hydrogels, cellulose and cellulose derivates, polyvinyldifluoride, polypropylenes, polyamides and polyimides. Most particularly this technique may be used to graft groups of formula (I) onto polyurethanes.

Such graft polymers may be obtained by conventional grafting methods as is described for example in our earlier patent application PCT/GB92/01580 the contents of which are incorporated herein by reference.

Graft polymers produced in this way may then be used to treat or coat a substrate according to the present invention. Alternatively in some cases such polymers may be moulded to form a bulk material rather than being used to treat a substrate.

Such grafted polymers may be used in the manner described in our earlier patent application PCT/GB92/01580.

B3 Further polymers of the invention are crosslinked copolymers obtainable by copolymerising a neutral diluent monomer or monomers, a polymerisable monomer or monomers containing a zwitterionic group Z and a bifunctional or trifunctional crosslinking agent.

Preferred monomers containing a group of formula (I) are those of formula (XII) or (XIII) as hereinbefore defined.

Preferred diluent monomers include alkyl (alk)acrylates, dialkylamino alkyl (alk)acrylates, alkyl(alk)acrylamides, hydroxyalkyl (alk)acrylates, N-vinyl lactams, styrene, substituted styrene derivatives; and mixtures thereof, preferably containing 1 to 4 carbon atoms in the said alkyl groups and moieties. More especially preferred as diluent monomers are vinylpyrrolidone, 2-hydroxyethylmethacrylate, methylmethacrylate and mixtures thereof.

Conventional crosslinking agents may be used. Examples of suitable crosslinking comonomers include alkane diol or triol di- or tri(alk)acrylates, eg (meth)acrylates, preferably containing 1 to 8 carbon atoms in the diol or triol residue; alkylene di- or tri-(alk) acrylamides, e.g. (meth)acrylamides, preferably containing 1 to 6 carbon atoms in the alkylene group and di- or tri-vinyl compounds such as di- or tri-vinyl benzene compounds. Particular examples of crosslinking agents include ethyleneglycoldimethacrylate, tetraethyleneglycol dimethacrylate, trimethylolpropanetrimethacrylate and N,N-methylenebisacrylamide.

Such copolymers may be obtained by conventional polymerisation techniques for the production of cross-linked copolymers as is described, for example in our earlier patent application WO-A-92/07885. The copolymers may be useful in the form of hydrogels for the production of contact lenses which are subject to reduced protein deposition.

B4 Further polymers of the invention are polyurethanes obtainable by the reaction of an aliphatic or aromatic di- or polyisocyanate and a diol or polyol having at least two hydroxyl groups capable of reacting with a isocyanate group and having the residue of at least one further hydroxyl group present as a zwitterionic group Z.

Such polyurethane polymers may be used in the fabrication of materials, having improved biocompatibility, using conventional techniques such as moulding. These polymers may be obtained in conventional manner as is for example described in our earlier patent application WO-A-86/02933 the contents of which are incorporated herein by reference.

B5. Further polymers of the invention are polyesters derived from a glycerol having the residue of one of the hydroxyl groups present as a zwitterionic group Z and at one di- or poly-functional acid or acid derivative thereof.

Preferred polyesters include repeating units of the formula (XXI)

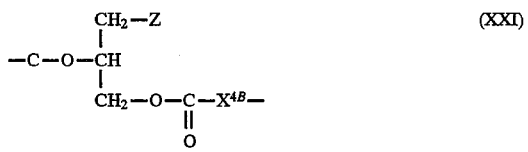 (XXI)

in which Z is as hereinbefore defined and $X^{4B}$ is a straight or branched $C_{1-15}$ alkylene or $C_{2-15}$ alkenylene group. Preferably such polymers are linear.

Such polyesters may be used to form materials using conventional techniques such as moulding. The polymers may be obtained in conventional manner as is described for example in our earlier patent application WO-A-88/00956 the contents of which are incorporated herein by reference.

B6. The present invention further provides a plastics material which comprises a polymer and a lipid which comprises a zwitterionic group Z.

In such a material, the lipid may be used as an additive for the polymer and in addition it may serve to improve the biocompatibility of the polymer. A wide variety of polymers may be used.

Preferably, such a lipid is a phospholipid containing a zwitterionic group Z, and most preferably, an analogue of a fatty acid diester of phosphatidyl choline of formula (VI).

Such materials may be produced in a manner analogous to that described in WO-A-87/02684. They may be used to provide articles comprising them in conventional manner.

A variety of materials comprising a surface having pendant zwitterionic groups Z may be used to provide a surface having improved biocompatibility, haemocompatibility and/or ocular compatibility. In particular such materials may show minimal interaction with biological systems such as blood, urine, tear films or tissue fluid. Such surfaces exhibit reduced tendency for example to protein adhesion or interaction with blood cells such as platelets at the surface or microorganisms, such as bacteria. Such a surface may be provided by treating, for example coating, a surface with a compound containing a group zwitterionic group Z or by providing a bulk materials which comprises zwitterionic groups Z.

In a particular aspect, the present invention provides a process for producing a material of the present invention which comprises (a) treating a surface of a substrate with a compound containing a zwitterionic group Z, or using a compound containing a zwitterionic group Z to produce a material comprising pendant groups Z at the surface and in the bulk of the material.

When a substrate is treated with a compound containing a zwitterionic group Z, the nature of the treatment used will depend upon the nature of the substrate.

Compounds containing zwitterionic groups Z which bind to the substrate by physisorption are particularly suitable for coating hydrophobic surfaces, e.g. polyethylene, polypropylene and polytetrafluoroethylene (PTFE) surfaces.

Hydrophilic surfaces may be rendered hydrophobic and suitable for coating with such compounds by known methods (see for example "Chemical Reactions of Polymers" Ed. E. M. Fettes, 1964, Interscience, London).

Treatment with such a compound is generally carried out by coating the surface with a solution or dispersion of the compound, generally in an alcoholic, aqueous, organic or halogenated solvent or a mixture thereof, e.g. methanol, ethanol, dichloromethane or other haloalkanes. The treatment is generally carried out at ambient or elevated temperature, such as from 5° to 150° C., preferably 25° to 75° C.

Compounds containing a zwitterionic group Z and a group capable of binding to a surface covalently are particularly suitable for treating substrates having functional groups, such as hydroxyl, carboxyl or amino groups.

Where necessary the surface of the substrate may be functionalised prior to treatment. For surfaces which do not have functional groups it may be necessary to introduce these groups at the surface before treatment. This can be effected by known etching or derivatising techniques, such as plasma discharge, which introduce the appropriate surface functionality (see for example "Chemical Reactions of Polymers" Ed. E. M. Fettes, 1964, Interscience, London).

In certain cases it is also necessary to activate functional groups at the surface of the substrate and/or the reactive groups of the polymer of the invention. This may be achieved by known means using a known activating agent for example a carbodiimide such as 1-ethyl-3-(3-dimethylaminopropyl)carbodiimide. Other suitable activating agents are disclosed in "Methods in Enzymology, volume 135, Immobilised Enzymes and Cells, part B", Ed. K. Mosbach, Academic Press Inc, N.Y., 1987.

Treatment with such a compound is generally carried out by treating the surface with a solution of the compound generally an alcoholic, aqueous alcoholic or aqueous solution. The treatment is generally carried out at a temperature from −5° to 50° C., for from 0.1 to 24 hours and at a pH from 2 to 13.

Materials having a surface comprising pendant zwitterionic groups Z can be used as a construction material for devices having many applications where microorganism adhesion can produce problems. One specific application is in relation to implants or prostheses for the human or animal body, particularly where these implants or prostheses are to come into direct physical contact with microorganisms. They can also be used in the construction of bioseparation membranes and other devices that are to be brought into contact with fluids containing microorganisms on an extracorporeal basis.

Where a material comprising zwitterionic groups Z in both the surface and bulk of the material is to be fabricated, then this may be performed using known conventional methodology for the fabrication of such materials, for example by the polymerisation, or copolymerisation of a polymerisable compound containing a zwitterionic group Z and optionally using known moulding or shaping techniques.

The present invention also relates to a process for producing a shaped article which comprises shaping an article from material comprising a surface having pendant zwitterionic group Z. It further relates to a shaped article comprising a surface having pendant groups comprising a zwitterionic group Z.

In addition, the present invention can be used to provide finished devices such as implants, prostheses, membranes, catheters, contact lenses and many other articles with improved biocompatibility.

The invention thus also provides a finish device having a surface having pendant zwitterionic groups Z. When the present invention provides a material which is then used in the construction of a finished device, it may be necessary to take precautionary steps to ensure that the surface is not damaged and the effectiveness of the treatment is not reduced before the finished device is produced. Such a device may be fabricated using known conventional methodology.

The present invention will now be illustrated by the following Examples.

EXAMPLES

The following assays were used to evaluate coatings of compounds according to the present invention.

Protein adsorption using an enzyme immunoassay

The assay determines absorption of human fibrinogen at a surface. This protein is representative of protein which is typically adsorbed at a surface. The assay can be readily modified to determine the absorption of other proteins.

Polyethylene tubing was coated with a sample and human plasma (5 ml) was pumped through the tubing using a Watson-Marlow multi-head peristaltic pump (lowest setting). The tubing was then washed by pumping through phosphate buffered saline (PBS) (x2). A solution containing antibodies specific to human fibrinogen (5 ml) was then pumped through followed by a further wash of PBS (x2). A conjugate of horseradish peroxidase and a second antibody specific to the first fibrinogen-specific antibody (5 ml) was passed through followed by a further wash of PBS (x2). O-Phenylene diamine in phosphate-citrate buffer (5 ml), (0.8 mg/ml) was passed through and the adsorption at 450 nm was read using a microplate reader.

Results are calculated as the percentage reduction in adsorption at 450 nm compared to an untreated sample of polyethylene tubing. As a control for non-specific binding of antibody to the samples each sample was also incubated with non-specific antibody.

Activated Platelet Study

Blood was collected from a healthy adult volunteer using the double syringe method where the first 5ml of blood is discarded. The blood was collected into tri-sodium citrate (32 g/l) in the proportion of 9 volumes to 1 volume citrate in plastic tubes. The samples were kept at room temperature on a spiral mixer until used.

Samples of polyethylene ribbon were treated with sample compound as described below and untreated polyethylene ribbon were used as controls.

Half of the test samples were incubated with citrated blood (200 µl) and the remainder were incubated with EDTA-treated blood on a phase shaker for 30 minutes before washing in PBS four times. Platelet activation was measured in a manner similar to that described above for detection of proteins by enzyme immunoassay using antibodies against GMP140 to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.

Example 1

1,2-dihexadecyl-3-{[hydroxyphosphinyl)oxy]-N,N,N trimethylhexaminium hydroxide, inner salt}-glycerol

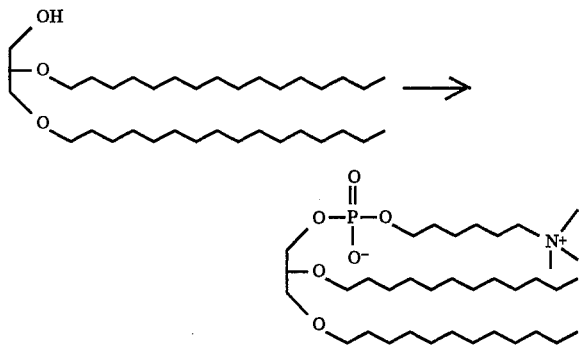

1,2-Dihexadecyl glycerol (0.50 g, 0.924 mmol) [prepared as described in Reference Example 1 which follows] was dissolved in anhydrous ether (10 ml) and triethylamine (0.190 g, 1.88 mmol) was added. The solution was stirred at room temperature under nitrogen for 30 minutes. Crude 6-(bromohexyl)-1-dichlorophosphate (0.502 g, 1.88 mmol) [prepared as described in Reference Example 2, which follows] in anhydrous ether (5 ml) was added dropwise. The reaction mixture was stirred at room temperature for 12 hours. Triethylamine (0.190 g, 1.88 mmol) and water (1 ml) were added to the reaction mixture which was then refluxed for 3 hours. After cooling the aqueous layer was extracted with ether (3 ml×3). The combined ethereal layers were dried (sodium sulphate) and rotary evaporated to yield a solid which was dried under vacuum. The solid was dissolved in dry chloroform (40 ml) and trimethylamine (1.50 g, 25.4 mmol) in acetonitrile (20 ml) was added and the reaction was stirred at 80° C. under a nitrogen atmosphere in a sealed vessel for 48 hours. After cooling the solvents were removed by rotary evaporation and the residue was purified by column chromatography eluted using chloroform:methanol:25% aqueous ammonia (690:270:64). Fractions containing the product were evaporated to dryness to give 1,2-dihexadecyl-3-{[hydroxyphosphinyl) oxy]-N,N,N trimethylhexaminium hydroxide, inner salt}-glycerol (362 mg, 0.475 mmol) 51% yield.

$^1$H-nmr (300 MHz, CDCl$_3$), 0.88 (6H, t), 1.26 (52H, m), 1.48 (8H, m), 1.59 (2H, m), 1.60 (2H, m), 3.25 (9H, s), 3.43 (5H, m), 3.52 (4H, m), 3.81 (4H, m).

Mass spectrum (FAB+ve ion) M+1=763. This compound when coated on polyethylene tubing in accordance with Example 7 showed a reduction in fibrinogen adsorption of 92%.

Reference Example 1

(a) 1-Trityl glycerol

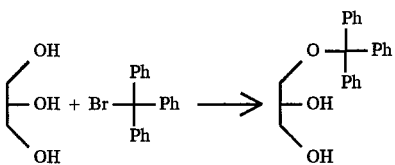

Glycerol (5.7 g, 61.9 mmol) was added to a solution of trityl bromide (20.0 g, 61.9 mmol) in dry dichloromethane (100 ml) and dry pyridine (100 ml). The reaction was stirred under an inert atmosphere at room temperature for 17 hours. The reaction mixture was then washed with water (100 ml×3) and brine (100 ml). The organic layer was dried (sodium sulphate) and the solvent removed by rotary evaporation to yield an amorphous solid. The solid was dissolved in hot benzene (150 ml), hexane (150 ml) was added and the solution was allowed to stand at room temperature for 12 hours. The resultant crystals were collected and dried (9.20 g, 44%). The mother liquors were evaporated and the resultant solid was crystallised again from hot benzene (100 ml) and hexane (100 ml) to yield further product (5.0 g, 24%).

Total yield (14.2 g, 69%).

$^1$H-nmr (200 MHz, CDCl$_3$), 3.21 (2H, m), 3.65 (2H, m), 3.85 (1H, m), 7.4 (15H, m).

(b) 1,2-dihexadecyl-3-trityl glycerol

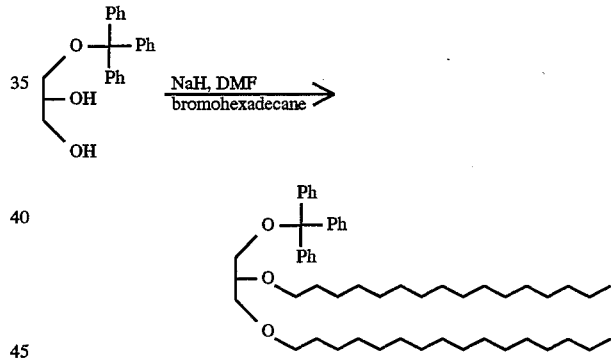

Sodium hydride (prewashed with hexane, 60% oil dispersion, 0.79 g, 32.89 mmol) was stirred in dry dimethyl formamide (50 ml) under a stream of nitrogen. 1-trityl glycerol (5.0 g, 14.95 mmol) in dry dimethyl formamide (50 ml) was added carefully. The reaction was stirred at room temperature for 30 minutes before 1-bromohexadecane (9.13 g, 29.90 mmol) was added and the reaction was stirred at room temperature under a nitrogen atmosphere for 12 hours. The reaction mixture was carefully partitioned between dichloromethane (100 ml) and water (100 ml×3). The organic layer was washed successively with saturated NaHCO$_3$ (100 ml) and brine (100 ml), dried over sodium sulphate and evaporated to yield the crude product, which was purified by column chromatography eluting with (40–60) light petroleum: ethyl acetate (230:20). Fractions containing product were evaporated to dryness to give 1,2-dihexadecyl-3-trityl glycerol (8.00 g, 10.21 mmol) 68% yield $^1$H-nmr (300 MHz, CDCl$_3$), 0.88 (6H, t), 1.26 (52H, m), 1.50 (4H, m), 3.16 (2H, d), 3.39 (2H, t), 3.51 (5H, m), 7.26 (10H, m), 7.47 (5H, m).

Mass spectrum (FAB+ve ion) M+1=782.

(c) 1,2-Dihexadecyl glycerol

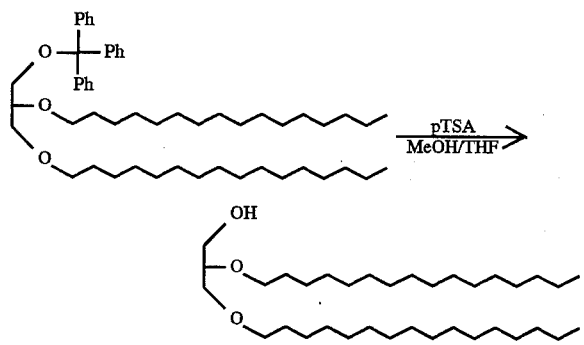

1,2-dihexadecyl, 3-trityl glycerol (8.00 g, 10.21 mmol) was dissolved in methanol:tetra-hydrofuran 2:1 (150 ml). p-Toluene sulphonic acid (ca 0.6 g) was added and the reaction was stirred at room temperature for 12 hours. The solvents were removed by rotary evaporation and the residue was partitioned between chloroform (100 ml) and water (100 ml×3). The organic layer was washed with brine (100 ml), dried (sodium sulphate) and rotary evaporated to yield the crude product which was purified by column chromatography eluting with solvent ranging from (40–60) light petroleum to (40–60) light petroleum:ethyl acetate (230:20). Fractions containing product were combined and rotary evaporated to yield 1,2-dihexadecyl glycerol (3.00 g, 5.54 mmol) 54% yield.

$^1$H-nmr (300 MHz, CDCl$_3$), 0.88 (6H, t), 1.26 (52H, m), 1.56 (4H, m), 3.41–3.74 (9H, m).

$^{13}$C-nmr (50 MHz, CDCl$_3$), 14.1, 22.7, 25.8, 26.1, 29.7, 31.9, 63.0, 70.4, 70.9, 71.8, 78.4.

Mass spectrum (FAB+ve ion) M+1=542.

Example 2

2-(Methacryloyloxyethyl)-6'-(trimethylammoniumhexyl) phosphate, inner salt

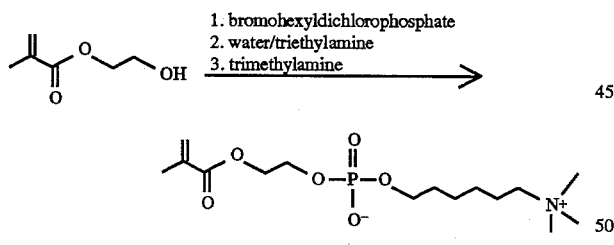

6-(Bromohexyl)-1-dichlorophosphate (7.22 g, 24.23 mmol) [prepared as described in Reference Example 2] in anhydrous ether (20 ml) was added to a solution of hydroxyethylmethacrylate (3.0 g, 23.00 mmol) in anhydrous ether (40 ml) and triethylamine (2.45 g, 24.23 mmol) at −20° C. The reaction was stirred at −20° C. under a nitrogen atmosphere for 3 hours. The reaction was allowed to warm to room temperature and triethylamine (2.45 g, 24.23 mmol), water (1 ml) and di-t-butyl cresol (ca 10 mg) were added. The reaction was stirred at room temperature for 2 hours. The aqueous layer was extracted with ether (5 ml×3) and the combined ethereal layers were dried (sodium sulphate) and the solvent removed by rotary evaporation to yield an oil that was dried under vacuum. The residue was dissolved in dry acetonitrile (20 ml) and trimethylamine (3.0 g, 50.8 mmol) in dry acetonitrile (30 ml) was added with di-t-butyl cresol (ca 10 mg). The reaction was stirred at 40° C. under a nitrogen atmosphere in a sealed vessel for 48 hours. After cooling the solvents were removed by rotary evaporation and the residue was purified by column chromatography eluted using methanol:water (9:1). Fractions containing the product were evaporated to dryness to give 2-(methacryloyloxyethyl)-6'-(trimethylammoniumhexyl) phosphate, inner salt (2.9 g, 8.65 mmol) 37%. This compound is referred to in subsequent examples as compound A.

$^1$H-nmr (200 MHz, CDCl$_3$ with trace CD$_3$OD), 1.46 (4H, m), 1.63 (2H, m), 1.80 (2H, m), 1.95 (3H, s), 3.17 (9H, s), 3.39 (2H, m), 3.86 (2H, q), 4.07 (2H, q), 4.34 (2H, t), 5.59 (1H, s), 6.13 (1H, s).

Reference Example 2

6-Bromohexyl-1-dichlorophosphate 6-Bromohexan-1-ol (5.90 g, 32.6 mmole) in dry dichloromethane (30 ml) was added dropwise to phosphorus oxychloride (5.0 g, 32.6 mmole) in dry dichloromethane (30 ml). Nitrogen was bubbled through the reaction mixture for four hours. The solvent was removed by rotary evaporation to yield 6-bromohexyl-1-dichlorophosphate, 9.70 g, 32.6 mmole, 100% yield.

$^1$H-nmr (200 MHz, CDCl$_3$), 1.48 (4H, m), 1.85 (4H, m), 3.41 (2H, t), 4.31, 4.38 (2H, dr).

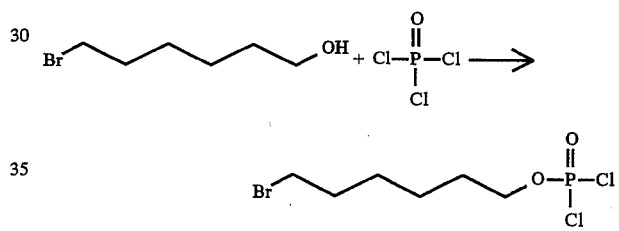

Example 3

1-[(2-Hydroxyethoxyhydroxyphosphinyl)oxy]-N,N,N-trimethyl undecylaminium hydroxide, inner salt.

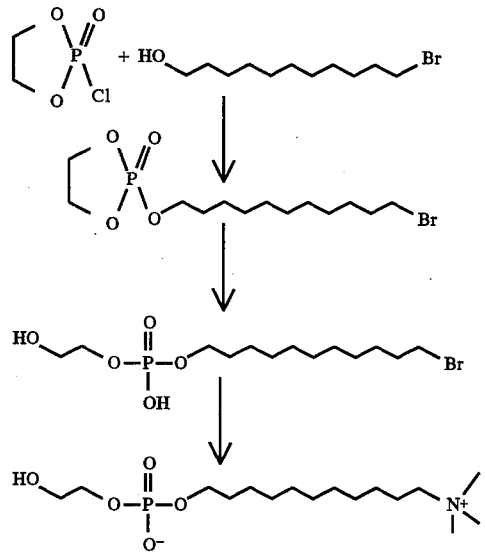

Triethylamine (1.21 g, 11.9 mmole) was added to 11-bromoundecan-1-ol (3 g, 11.9 mmole) in diethyl ether (40 ml) 2-chloro-2-oxo-1,3,2-dioxaphospholane (1.7 g, 11.9 mmole) was added over a minute. After three hours stirring at ambient temperature, further 2-chloro-2-oxo-1,3,2-dioxaphospholane (1.7 g, 11.9 mmole) was added and the material left for a further three hours. The solid was removed by filtration and the solvent evaporated. Water/acetone (1:1, 10 ml) was added to the residue and after two hours, the solvents were evaporated and the residue azeotroped to a white powder with benzene.

An excess of trimethylamine/acetonitrile (40 ml) was added and the mixture placed in a sealed vessel and heated at 70° C. for five days. On cooling a solid was precipitated on the side of the reaction vessel. The liquors were decanted, evaporated to a crude solid and chromatographed on silica (30 g) eluting with methanol. Fractions containing product were combined and evaporated to give 11-[(2-hydroxyethoxyhydroxyphosphinyl)oxy]-N,N,N-trimethyl undecylaminium hydroxide, inner salt, 270 mg, 0.76 mole, 7% yield. Tlc (methanol:water, 9:1), single spot, sprayed positive with Dragendorff and molybdate sprays.

$^1$H-nmr (300 MHz, CD$_3$OD), 1.35 (14H, m), 1 60 (2H, m), 1.78 (2H, m), 3.11 (9H, s), 3.30 (2H, m), 3.66 (2H, t), 3.87 (4H, m).

Example 4

1,2-Dipalmitoyl 3-[(hydroxyphosphoryl)oxy]-N,N,N, trimethyl undecylaminium hydroxide, inner salt}glycerol

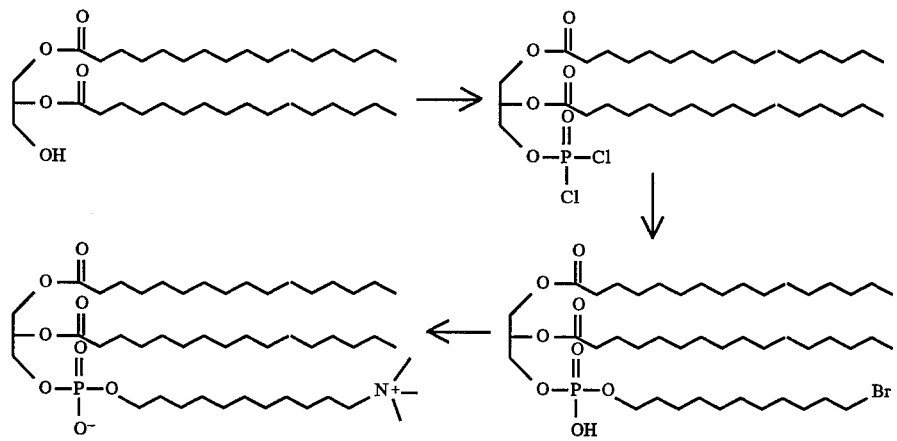

1,2-dipalmitoyl glycerol (300 mg, 0.53 mmole) and triethylamine (53 mg, 0.53 mmole) in dried dichloromethane (80 ml) were added dropwise to a solution of freshly distilled phosphorus oxychloride (81 mg, 0.53 mmole) in dichloromethane (20 ml) under nitrogen. The mixture was heated to 65° C. for 30 minutes, cooled to ambient temperature and pyridine (0.27 ml) and 11-bromoundecan-1-ol (132 mg, 0.53 mmole) was added. The mixture was stirred at ambient temperature for five hours. Water (2 ml) was added and the mixture was stirred for ten minutes. The aqueous layer was removed and the organic phase was successively washed with equal volumes of water, hydrochloric acid (1 M, x2) and brine, dried over sodium sulphate and evaporated to a waxy solid which was partially purified by column chromatography on silica gel (35 g), eluting with dichloromethane:methanol (9:1).

The crude product (410 mg) was dissolved in dichloromethane (10 ml) and was heated in a sealed vessel at 70° C. for 18 hours together with a solution of trimethylamine (1 g, 17 mmole) in dichloromethane (40 ml). After cooling a white precipitate was observed which was isolated by filtration, dissolved in chloroform (50 ml) and extracted with water (50 ml) and brine (50 ml). After drying over sodium sulphate the crude product was chromatographed on silica gel (30 g), eluting with chloroform:methanol:ammonia (25%) (690:270:49). Pure 1,2-dipalmitoyl 3-[(hydroxyphosphoryl)oxy]-N,N,N, trimethyl undecylaminium hydroxide, inner salt}glycerol was obtained by evaporation of the relevant fractions to give 15 mg, 0.02 mmole, 4% yield, which was shown to stain positively with molybdate and Dragendorf spray reagents.

Mass spectrum: (FAB+ve ion m-nitrobenzyl alcohol matrix) M+1=861.

A further batch of crude material (0.4 g) was isolated from the column.

Example 5

A piece of polyethylene tubing (1.6×300 mm) was washed with ethanol (passed through a 2 μm filter, 400 μl at 60° C.) for one minute. After decanting the ethanol a solution of the compound prepared in Example 1 in ethanol (0.30 ml) was placed in the tube at 60° C. After leaving for one minute the solution was removed and the tubing dried under nitrogen.

The coated sample showed a 92% reduction in fibrinogen absorption as compared to uncoated tubing using the assay procedure described above.

Example 6

Polyethylene ribbon strips (102×25.5 mm) were washed with ethanol at 20° C. These strips were attached to a piece of PVC tubing (10 mm×60 mm) which was mechanically lowered (25 mm sec$^{-1}$) into a bath containing the compound prepared in Example 4 in ethanol (12.9 ml) at 65° C., left for one minute and then removed at a speed of 4 mm/sec. The samples were dried in a laminar flow tent.

The coated sample showed a 90% reduction in platelet activation compared to an uncoated sample, using the assay procedure described by E. J. Campbell et al, M.R.S. symp. proc. vol. 252, pp 229–236, (1992).

Example 7

Copolymer of 2-(methacryloyloxyethyl) -6'-(trimethylammonium hexyl)phosphate, inner salt and lauryl methacrylate

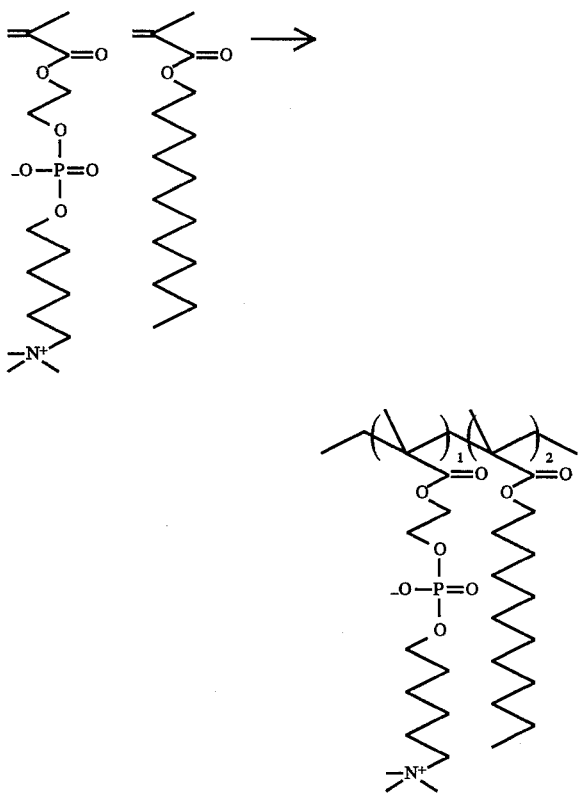

A solution of methacrylate monomer (compound A) (4.92 g, 12.7 mmole) in dry isopropanol (60 ml) was treated with a solution of freshly distilled lauryl methacrylate (6.47 g, 25.4 mmole) in dry ethyl acetate (16 ml). Nitrogen was bubbled through the mixture for five minutes before AIBN (20 mg) in ethyl acetate (2.5 ml) was added and the stirred mixture heated to 62° C. under nitrogen for forty hours. The mixture was cooled to 40° C., filtered through filter paper and washed through with isopropanol (8 ml). The solvents were removed by evaporation and the coloured residue was dissolved in dichloromethane (37 ml) and methanol (4 ml) and dripped slowly (over ca. one hour) into a beaker containing vigourously stirred acetone (530 ml). A gummy deposit was formed on the surface of the vessel, which after decanting the solvent, and washing the residue with further acetone (150 ml), was dried under vacuum for 16 hours. This was dissolved in dichloromethane (30 ml) and methanol (10 ml) and dripped slowly into a stirred solution of acetone (ca. 600 ml. A gum was slowly deposited which was left at 4° C. for 64 hours before the acetone was decanted, the residue washed with acetone (150 ml) prior to dissolving it in methanol/dichloromethane and evaporating and then drying under vacuum to give polymer, 2.86 g.

$^1$H-nmr (300 MHz, CDCl$_3$/CD$_3$OD, 1:1), 0.75–1.15 (15H, m), 1.15–1.55(46H, m), 1.55–2.10(10H,m), 3.20(9H, s), 3.25–4.40 (12, m) $^{13}$C-nmr The polymer was coated onto polyethylene ribbon in accordance with Example 5, but from a solution at 3 mg/ml and also at 10 mg/ml. These samples showed a reduction in fibrinogen adsorption of 74% and 85% respectively. The polymer was coated onto polyethylene ribbon, in accordance with Example 6, but from solutions at 3 mg/ml and 10 mg/ml. These samples showed a reduction in the activation of platelets of 41% and 50% respectively.

We claim:

1. A method for preparing a coated substrate, comprising the steps (a) and (b) of
   (a) coating onto a surface of a substrate a solution or dispersion in a solvent of a polymer formed by polymerizing a monomer selected from compounds of formula (XII) and (XIII):

(XII)

(XIII)

said polymer being obtained by copolymerizing a polymerizable comonomer containing a zwitterionic group Z and a second comonomer containing a group that binds the copolymer to a surface, or by polymerizing a polymerizable monomer containing both a zwitterionic group Z and a group that binds the polymer to a surface, wherein in formula (XII) and (XIII):

$R^{11}$ is hydrogen or a $C_1$-$C_4$ alkyl group;

L is —O— or —NR$^{12}$— wherein R$^{12}$ is selected from the group consisting of hydrogen, $C_1$-$C_4$ alkyl, and —B—Z$^B$, wherein B and Z$^B$ are as defined below:

K is selected from the group consisting of —(CH$_2$)$_p$OC(O)—, —(CH$_2$)$_p$C(O)O—, —(CH$_2$)$_p$OC(O)O—, —(CH$_2$)$_p$NR$^{13}$—, —(CH$_2$)$_p$NR$^{13}$C(O)—, —(CH$_2$)$_p$C(O)NR$^{13}$—, —(CH$_2$)$_p$NR$^{13}$C(O)O—, —(CH$_2$)$_p$OC(O)NR$^{13}$—, —(CH$_2$)$_p$NR$^{13}$C(O)NR$^{13}$— wherein the R$^{13}$ groups are the same or different, —(CH$_2$)$_p$O—, —(CH$_2$)$_p$SO$_3$—, and a covalent bond, wherein p is from 1 to 12 and R$^{13}$ is hydrogen or a $C_1$-$C_4$ alkyl;

B is selected from the group consisting of a covalent bond, straight and branched alkylene, oxaalkylene and oligo-oxaalkylene groups, each containing up to 12 carbon atoms, and each optionally containing one or more fluorine atoms; and Z$^B$ is a zwitterionic group selected from the group consisting of Z and groups of formulae XIV, XV and XVI wherein Z is a group of formula (II)

(II)

wherein:

$X^1$ and $X^2$, which are the same or different, are selected from the group consisting of —O, —S—, —NH—, and a covalent bond; and $W^+$ is a cationic group selected from the group consisting of —W$^1$—N$^+$R$^3$$_3$, —W$^1$—P$^+$R$^{3a}$$_3$, —W$^1$—S$^+$R$^{3a}$$_2$ and —W$^1$—Het$^+$, wherein $W^1$ is selected from the group consisting of an alkylene having at least 5 carbon atoms, and optionally containing one or more ethylenically unsaturated double or triple bonds, a disubstituted-aryl, an aryl alkylene, an alkylene aryl alkylene, a disubstituted cycloalkyl, an alkylene cycloalkyl, a cycloalkyl alkylene, and an alkylene cycloalkyl alkylene, any one of which optionally contains one or more fluorine substituents and/or one or more functional groups, the R³ groups are the same or different, and each is hydrogen or an alkyl having from 1 to 4 carbon atoms, wherein two of the R³ groups are optionally bonded together with the nitrogen atom to which they are attached to form a heterocyclic ring containing from 5 to 7 atoms, or the three R³ groups are optionally bonded together with the nitrogen atom to which they are attached to form a fused ring structure containing from 5 to 7 atoms in each ring, and optionally one or more of the R³ groups is substituted by a hydrophilic functional group, the $R^{3a}$ groups are the same or different and each is $R^3$ or $-OR^3$, where $R^3$ is as defined above; and Het is selected from the group consisting of an aromatic nitrogen-containing ring, an aromatic phosphorus-containing ring, and an aromatic sulphur-containing ring, (ii) formula (XIV)

$$\begin{array}{c} CH_2-Z \\ | \\ -(O)_2-CH \\ | \\ CH_2-O-R^{14} \end{array} \quad (XIV)$$

wherein:

$R^{14}$ is hydrogen or a group of formula $-C(O)B^1R^{14a}$ wherein $R^{14a}$ is hydrogen or methyl;

$B^1$ is selected from the group consisting of a covalent bond, straight and branched alkylene, oxaalkylene and oligo-oxaalkalyene;

if B is a covalent bond and K is other than a covalent bond, z is 0, and otherwise, when B is a covalent bond, z is 1;

Z is as defined above, (iii) formula (XV)

$$\begin{array}{c} CH_2-Z \\ | \\ CH-O-R^{14} \\ | \\ -(O)_2-CH_2 \end{array} \quad (XV)$$

wherein $R^{14}$, $B^1$, z, and Z are as defined above, and (iv) formula (XVI)

$$\begin{array}{c} CH_2-OR^{14} \\ | \\ CH-Z \\ | \\ -(O)_2-CH_2 \end{array} \quad (XVI)$$

wherein $R^{14}$, $B^1$, z, and Z are as defined above; and (b) evaporating the solvent to obtain a coating of said polymer on the surface of said substrate.

2. The method according to claim 1, wherein each R³ is unsubstituted.

3. The method according to claim 1, wherein each R³ is methyl.

4. The method according to claim 1, wherein Het is an aromatic nitrogen-containing ring.

5. The method according to claim 4, wherein said aromatic nitrogen-containing ring is pyridine.

6. The method according to claim 1, wherein $Z^B$ is a group Z.

7. The method according to claim 1, wherein B is a straight alkylene group having up to 12 carbon atoms.

8. The method according to claim 8, wherein B is ethylene.

9. The method according to claim 1, wherein said copolymerising to obtain the polymer consists of copolymerising a polymerisable comonomer containing a zwitterionic group Z and a second comonomer containing a group that binds the polymer to a surface.

10. The method according to claim 1, wherein said group that binds the polymer to a surface binds the polymer in a manner selected from the group consisting of physisorption, covalent binding and ionic binding to a reactive group at the surface.

11. The method according to claim 10, wherein said comonomer is selected from compounds of formulae (XVIIA) and (XVIIB)

$$\begin{array}{c} R^{15} \\ | \\ CH_2=C-C-L^1-G \\ \parallel \\ O \end{array} \quad (XVIIA)$$

$$\text{(XVIIB)}$$
(4-vinylphenyl)–$K^1$–G wherein $R^{15}$ is hydrogen or a $C_{1-4}$ alkyl group, $L^1$ is $-O-$ or $-NR^{16}$, wherein $R^{16}$ is selected from the group consisting of hydrogen, $C_{1-4}$ alkyl, and $-G$ as defined below, $K^1$ is selected from the group consisting of $-(CH_2)_qOC(O)-$, $-(CH_2)_qC(O)-$, $-(CH_2)_qOC(O)O-$, $-(CH_2)_qNR^{17}-$, $-(CH_2)_qNR^{17}C(O)-$, $-(CH_2)_qC(O)NR^{17}-$, $-(CH_2)_qNR^{17}C(O)O-$, $-(CH_2)_qOC(O)NR^{17}-$, $-(CH_2)_qNR^{17}C(O)NR^{17}-$, wherein the $R^{17}$ groups are the same or different, $-(CH_2)_qO-$, $-(CH_2)_qSO_3-$, and, optionally in combination with B, a covalent bond, wherein q is from 1 to 12, $R^{17}$ is hydrogen or a $C_1-C_4$ alkyl, and G is selected from the group consisting of:

a) a reactive group that covalently binds to a surface;

b) a group that binds to a surface by physisorption; and c) an ionic group that binds to a surface by ionic interaction.

12. The method according to claim 11, wherein G is as defined in a), and is selected from the group consisting of alkylene, oxalkylene and oligo-oxaalkylene groups, terminating in a reactive group selected from the group consisting of aldehyde, hydroxyl, amino, carboxyl, epoxy, $-CHOHCH_2Hal$ wherein Hal is a halogen atom, succinimido, tosylate, triflate, imidazole carbonyl-amino and an optionally substituted triazine.

13. The method according to claim 11, wherein G is a group defined in b), and is selected from the group consisting of an alkyl containing 6 or more carbon atoms, an alkoxy-alkyl containing 6 or more carbon atoms, an (oligo-alkoxy) alkyl containing 6 or more carbon atoms, an alkyl containing 6 or more carbon atoms and substituted by one or more fluorine atoms, an alkoxyalkyl containing 6 or more carbon atoms and substituted by one or more fluorine atoms, an (oligo-alkoxy) alkyl group containing 6 or more carbon atoms and substituted by one or more fluorine atoms, and a siloxy group containing from 1 to 50 silicon atoms.

14. The method according to claim 13, wherein said comonomer is a compound of formula (XVIIA) as defined in claim 11.

15. The method according to claim 14, wherein G is an alkyl group containing 6 or more carbon atoms.

16. The method according to claim 14, wherein said second comonomer is lauryl methacrylate.

17. The method according to claim 11, wherein G is a group defined in c), and is an anionic group selected from the group consisting of carboxylate, sulphonate, hydrogenphosphate, and phosphate groups, or is a cationic group selected from the group consisting of quaternary ammonium and phosphonium groups.

18. A method for preparing a coated substrate according to claim 1, wherein the group B is an alkylene group comprising at least 7 carbon atoms.

19. A method for preparing a coated substrate according to claim 1, wherein the group B is ethylene.

20. A method for preparing a coated substrate according to claim 1, wherein $Z^B$ is of formula II in which $W^1$ is a straight-chain alkylene group having at least 7 carbon atoms.

21. A method for preparing a coated substrate according to claim 19, wherein $W^1$ is 1, 6-hexylene.

22. A method according to claim 15, wherein G is selected from a group that binds to a surface by physisorption, wherein the comonomer is a compound of formula (XVIIA); wherein B is a straight alkylene group having up to 12 carbon atoms; and wherein each of $X^1$ and $X^2$ is —O—.

23. A method according to claim 22, wherein $W^+$ is a group —$W^1$—$N^+R^3_3$, wherein each $R^3$ is an unsubstituted $C_{1-4}$ alkyl and wherein $W^1$ is an alklyene group of 6 or more carbon atoms.

24. A method according to claim 11, wherein $Z^B$ is a group Z, in which each of $X^1$ and $X^2$ is —O—, $W^+$ is —$W^1$—$N^+R^3_3$, wherein $W^1$ is as defined in claim 11, and each of the R3 groups is $C_{1-4}$-alkyl and wherein B is a straight alkylene group having up to 12 carbon atoms.

* * * * *